United States Patent [19]

Ife et al.

[11] Patent Number: 4,997,847

[45] Date of Patent: Mar. 5, 1991

[54] BIOLOGICALLY ACTIVE COMPOUNDS

[75] Inventors: Robert J. Ife, Stevenage; David G. Cooper; Robert A. Slater, both of Letchworth, all of England; Karlheinz Stegmeier, Heppenheim; Ernst-Christian Witte, Mannheim, both of Fed. Rep. of Germany

[73] Assignees: Smith Kline & French Laboratories Limited, Welwyn Garden City; Boehringer Mannheim GmbH, Mannheim, Fed. Rep. of Germany

[21] Appl. No.: 235,061

[22] Filed: Aug. 22, 1988

[30] Foreign Application Priority Data

Aug. 20, 1987 [GB] United Kingdom ............... 8719717
Oct. 30, 1987 [GB] United Kingdom ............... 8725540

[51] Int. Cl.$^5$ ............ A61K 31/38; A61K 31/34; A61K 31/275; A61K 37/44

[52] U.S. Cl. .................... 514/445; 514/471; 514/472; 514/522; 514/538; 514/562

[58] Field of Search ............ 549/65, 456; 562/430; 514/471, 445, 562, 472, 522, 538

[56] References Cited

FOREIGN PATENT DOCUMENTS 68968A 6/1982 European Pat. Off. .

Primary Examiner—Alan Siegel
Attorney, Agent, or Firm—Jeffrey A. Sutton; Stuart R. Suter; Edward T. Lentz

[57] ABSTRACT

The invention relates to phenylsulphonamidolkanoic acids which have thromboxane $A_2$ receptor antagonist activity.

5 Claims, No Drawings

BIOLOGICALLY ACTIVE COMPOUNDS

The present invention relates to the use of a class of ω-arylsulphonamidoalkanoic acids in the preparation of medicaments for the treatment of thromboxane mediated diseases, and to novel ω-arylsulphonamidoalkanoic acids.

Thromboxane $A_2$ ($TXA_2$) is a potent vasoconstricting and platelet aggregating agent which is formed in platelets and other tissues as a product of the "arachidonic acid cascade". $TXA_2$ is produced by the thromboxane synthetase catalysed conversion of protaglandin $H_2$ ($PGH_2$) which in turn is produced, via the intermediacy of prostaglandin $G_2$ ($PGG_2$), by the action of cyclooxygenase on arachidonic acid. The potency of $TXA_2$ is such that very small amounts can trigger serious biological consequences and it has been implicated in mediating pathophysiological actions in severe disorders such as circulatory shock and myocardial ischaemia.

One method of inhibiting the effects of thromboxane $A_2$ is through the selective antagonism of $TXA_2/PGH_2$ at the receptor level and various compounds have been reported as $TXA_2$ receptor antagonists, see for example U.S. Pat. No. 4,536,510 and EP 31954.

European Patent Application EP 68968A describes a class of arylsulphonamidoalkanoic acids as hypolipidaemic agents. One particular class of compounds disclosed in EP 68968A is represented by formula (A):

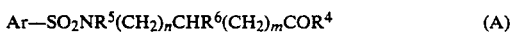

$$Ar-SO_2NR^5(CH_2)_nCHR^6(CH_2)_mCOR^4 \quad (A)$$

wherein Ar can be, inter alia, a phenyl ring having attached thereto the groups $R^1$, $R^2$ and $R^3$; or a thienyl ring bearing the group $R^1$; wherein $R^1$, $R^2$ and $R^3$ are the same or different and are hydrogen, halogen, $NO_2$, $NH_2$, $CF_3$, $C_{1-6}$alkyl, $C_{1-6}$alkoxy, $CO_2H$ or a $C_{2-7}$ ester thereof; the total $n+m+1$ is in the range from 3 to 11; and $R^4$ is OH, $C_{1-4}$alkoxy or a group $NR^8R^9$ wherein $R^8$ and $R^9$ are the same or different and are $C_{1-6}$alkyl or together with the nitrogen atom for a 5- or 6-membered heterocyclic ring; $R^5$ and $R^6$ are the same or different and are hydrogen, $C_{1-6}$alkyl or $C_{7-9}$aralkyl.

Preferred compounds are stated to be those wherein $n+m+1$ is 3, 5 or 10.

It has now been found that certain ω-aryl-sulphonamidoalkanoic acids have thromboxane $A_2$ antagonist activity. Such activity has been found to be particularly high in compounds with heptanoic, octanoic, nonanoic and decanoic acid side chains.

In a first aspect, therefore, the present invention provides the use of a compound of the formula (I):

$$RSO_2NR'BCO_2H \quad (I)$$

or a salt or ester thereof, wherein R is a phenyl, furan or thiophene ring optionally substituted by one or more substituents which are the same or different and are chosen from halogen, nitro, cyano, trifluoromethyl, $C_{1-4}$alkyl and $C_{1-4}$alkoxy: R' is hydrogen or $C_{1-4}$alkyl; and B is an acyclic hydrocarbon group having 4 to 11 linear carbon atoms, preferably at least 5 linear carbon atoms and most preferably at least 6 linear carbon atoms, any one or more of the linear carbon atoms of which are optionally substituted by one or two $C_{1-3}$alkyl groups; in the preparation of a medicament for the treatment of thromboxane mediated diseases.

The present invention also provides an advantageous class of novel compounds of the formula (I) wherein the group R is optionally substituted by one or two substituent groups which are the same or different and are chosen from halogen, nitro, cyano, trifluoromethyl, $C_{1-4}$alkyl and $C_{1-4}$alkoxy; and B is an acyclic hydrocarbon group having 6 to 9 linear carbon atoms, each linear carbon atom of B being optionally substituted by one or two $C_{1-3}$alkyl groups, but provided that when B is an unbranched alkylene group and R is a phenyl ring, the phenyl ring is either disubstituted or it has only one substituent which is chosen from halogen, nitro, cyano, trifluoromethyl, $C_{1-4}$alkoxy, o- or m-$C_{1-4}$alkyl and p-$C_{2-4}$alkyl.

By linear carbon atoms is meant those carbon atoms which form an unbranched chain between the sulphonamide nitrogen atom and the carboxyl group.

Particular optional $C_{1-3}$alkyl substituents are methyl and ethyl, preferably methyl.

The acyclic hydrocarbon group B can be an alkylene group or it can contain carbon-carbon multiple bonds such as double and triple bonds. The group can be a branched chain or straight chain group, for example a branched chain or straight chain alkylene group.

When the group B is a straight chain alkylene group, suitably it can be a group $(CH_2)_6$, $(CH_2)_7$, $(CH_2)_8$ or $(CH_2)_9$ but preferably it is $(CH_2)_7$, $(CH_2)_8$ or $(CH_2)_9$; and when the group B is a branched chain alkylene group, preferably it is $(CH_2)_5C(CH_3)_2$, $(CH_2)_6C(CH_3)_2$, $(CH_2)_7C(CH_3)_2$ or $(CH_2)_8C(CH_3)_2$.

The group R is suitably phenyl or a thiophene ring. Examples of substituents on the group R are chlorine, bromine, fluorine, nitro, methoxy and methyl.

When R is phenyl, it is preferred that any substituents are located at the 3- and/or 4-positions of the phenyl ring.

Preferred compounds are those wherein the 3-position of the phenyl ring is unsubstituted or is substituted by fluorine, chlorine, or bromine; and the 4-position of the phenyl ring is substituted by fluorine, chlorine, bromine, nitro, methoxy or methyl.

Particularly preferred compounds are those wherein the 3-position of the phenyl ring is unsubstituted or substituted by chlorine, and the 4-position is substituted by chlorine, bromine or methyl.

A particular sub-group of compounds is the group wherein B is $(CH_2)_7$, $(CH_2)_8$ or $(CH_2)_9$; R' is hydrogen and R is a phenyl ring wherein the 3-position of the phenyl ring is unsubstituted or substituted by chlorine, and the 4-position is substituted by chlorine, bromine or methyl.

When R is a thiophene or furan group, suitably it is a 2-furyl, 2-thienyl or 3-thienyl group, and preferably it is a 2-thienyl group optionally substituted at the 4-and/or 5-position of the thiophene ring, particularly the 5-position. Preferably the thiophene ring is monosubstituted and particularly the substituent is a 5-chloro, 5-bromo or 5-methyl group.

R' is preferably hydrogen.

Another class of novel compounds of the formula (I) according to the present invention is that class of compounds wherein B is a group $(CH_2)_yCR^cR^dCH_2$, wherein y is an integer from 2–9 and $R^c$ and $R^d$ are the same or different and each is a $C_{1-3}$alkyl group. Such compounds will be referred to hereinafter for convenience as the β-gem dialkyl compounds.

It is preferred that, with regard to the β-gem dialkyl compounds, y is 4–7, particularly 5. The groups $r^c$ and $R^d$ can be chosen from methyl, ethyl and propyl but preferably both are methyl.

Preferably the group R is a phenyl group.

Conveniently, the phenyl group R of the β-gem dialkyl compounds has up to two substituents defined hereinabove. Particular substituent groups are chlorine, bromine, fluorine, methyl, methoxy, nitro and trifluoromethyl.

Suitably the phenyl ring is monosubstituted and the substituent group is located at the para-position of the phenyl ring. Thus, for example, a particularly preferred substituent group is p-chloro.

Preferred novel compounds of the present invention include 8-(4-chlorobenzenesulphonamido)octanoic acid, 8-(4-chlorobenzenesulphonamido)-2,2-dimethyloctanoic acid, 9-(4-chlorobenzenesulphonamido)nonanoic acid, 8-(4-bromobenzenesulphonamido)octanoic acid, 8-(3,4-dichlorobenzenesulphonamido)octanoic acid, 8-(4-tolylsulphonamido)octanoic acid, 9-(4-bromobenzenesulphonamido)nonanoic acid, 8-(5-chloro-2-thienylsulphonamido)octanoic acid, 10-(4-chlorobenzenesulphonamido)decanoic acid, 8-(4-chlorobenzenesulphonamido)- 3,3-dimethyloctanoic acid and esters and pharmaceutically acceptable salts thereof.

Compounds of the formula (I) can form salts with bases and all such salts are within the scope of the invention. Preferred salts are carboxylate salts formed by interaction of the carboxylic acid group with an appropriate base.

Examples of carboxylate salts are alkali metal, alkaline earth metal and ammonium salts. Alkali and alkaline earth metal salts typically are formed by interaction of a carboxylic acid with a metal alkoxide or hydroxide whereas ammonium salts typically are formed by interaction of the carboxylic acid with the appropriate amine or the appropriate ammonium hydroxide.

It is preferred that the salts are pharmaceutically acceptable, although non-pharmaceuticals salts are also within the scope of the invention. Such salts can be converted into pharmaceutically acceptable salts or into the corresponding free acid.

Where compounds of formula (I) exist as solvates, for example hydrates and alcoholates, all such forms are within the scope of the invention.

Examples of esters of the compounds of the formula (I) include $C_{1-6}$alkyl esters and $C_{7-10}$aralkyl esters wherein the aryl ring is optionally substituted by one or more substituents, for example $C_{1-4}$alkyl, halogen, nitro and $C_{1-4}$alkoxy.

Preferred esters are $C_{1-4}$alkyl esters.

Compounds of the formula (I) can be prepared by the reaction of a compound of the formula (II):

$$E-B-Y \quad \quad (II)$$

with a compound of the formula (III):

$$RSO_2G \quad \quad (III)$$

wherein Y is $CO_2H$ or a group hydrolysable thereto; one of E and G is a group NHR' and the other is a leaving group displaceable by a group NHR' and R is as defined hereinbefore, and thereafter, where required, hydrolysing any hydrolysable group Y to give $CO_2H$.

Suitably the group hydrolysable to $CO_2H$ is a nitrile or an ester, for example a $C_{1-6}$alkyl or optionally substituted aralkyl ester such as benzyl.

Examples of leaving groups are halogens such as chlorine and bromine.

The reaction of a compound of the formula (II) with a compound of the formula (III) can be conducted in a polar solvent, usually aprotic and preferably dry, such as dry acetone, methylethylketone, dimethylformamide, pyridine or dichloromethane, with heating where required, for example at the reflux temperature of the solvent. The reaction typically is conducted in the presence of another base such as pyridine, an alkali metal carbonate such as potassium carbonate, or a trialkylamine such as triethylamine.

Alternatively, when G is a leaving group such as a halogen e.g. chlorine, the reaction can be conducted under Schotten-Baumann conditions, i.e. the reactants are stirred or shaken together in the presence of an aqueous alkali such as dilute sodium hydroxide.

General methods for preparing compounds of the formula (I) and chemical intermediates thereto are disclosed in EP 68968A.

Many amino acids of the formula (II) wherein E is NHR' can be obtained commercially and those that are not can be prepared by well known and conventional synthetic methods, for example by reaction of the corresponding compound of the formula (II) wherein E is a leaving group such as bromine, and Y is a group hydrolysable to $CO_2H$, e.g. an ester or nitrile thereof; with an alkali metal salt of phthalimide, such as the potassium salt, to give the ω-phthalimido compound. The phthalimido compound can then be deprotected by standard methods, for example by treatment with HCl to hydrolyse the group Y to give the carboxylic acid, and then by reaction with hydrazine, to remove the phthaloyl group to give the amine. This method of making amines is the well known Gabriel synthesis.

Compounds of the formula (II) wherein E is a leaving group can be prepared according to standard methods. For example, when it is desired to prepare a compound wherein B is a group $(CH_2)_nCR^1R^bCO_2H$; n is 4 to 10 and $R^a$ and $R^b$ are $C_{1-3}$alkyl groups such as methyl groups, such compounds can be prepared by reacting a compound $Br(CH_2)_nBr$ with ethylisobutyrate in the presence of a strong base such as lithium diisopropylamide (LDA), under conditions described in U.S. Pat. No. 4,579,862, or similar thereto.

Compounds of the formula (II) which contain a double or triple bond can be prepared according to methods described in Casey et al, Tetrahedron, 42, 5849 (1986) or methods closely analogous thereto.

Compounds of the formula (III) are commercially available or can be made according to standard methods, for example as described in EP 68968A.

The hydrolysis of a group Y to $CO_2H$ can be carried out according to conventional methods or methods analagous thereto. Thus, for example, both nitrile and ester groups can be hydrolysed in aqueous alkali such as aqueous sodium hydroxide. Typically such reactions are carried out using an alkanol such as ethanol as a co-solvent and, when the group Y is a nitrile group, it is usual to heat the reaction mixture, e.g. to reflux temperature.

In addition to the method described above, the compounds of the present invention can also be prepared by the hydrolysis and decarboxylation of compounds of the formula (IV):

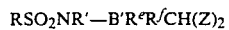
$$RSO_2NR'-B'R^aR^{/}CH(Z)_2 \quad \quad (IV)$$

wherein R and R' are as hereinbefore defined, $R^e$ and $R^f$ are the same or different and each is hydrogen or methyl, B' is an acyclic hydrocarbon group having 2 to 9 linear carbon atoms, and Z is a $C_{1-4}$alkoxycarbonyl group or a nitrile group. This method is particularly suitable for preparing compounds wherein B' is a straight chain alkylene group and $R^e$ and $R^f$ are both methyl.

Hydrolysis and decarboxylation suitably is achieved by heating the compound of the formula (IV) in an appropriately acidic or basic aqueous solvent. For example, when Z is $C_{1-4}$alkoxycarbonyl such as ethoxycarbonyl, the compound of the formula (IV) can be hydrolysed and decarboxylated by heating at reflux in the presence of aqueous alkali such as sodium hydroxide.

Compounds of the formula (IV) can be prepared by the reaction of a metal salt, such as the sodium salt, of a compound of the formula (III) wherein G is a group NHR', with a compound of the formula (V):

$$Br-B'R^eR^fCH(Z)_2 \qquad (V),$$

wherein the carbon atom to which Br is attached is saturated, in a polar aprotic solvent such as dimethylformamide, suitably with heating.

Compounds of the formula (V) can be prepared according to the methods illustrated in Reaction Scheme 1 or methods analogous thereto.

compound of the formula (I) and a pharmaceutically acceptable carrier.

The compositions can be administered in standard manner, for example orally, parenterally, transdermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavoring or coloring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene gly-

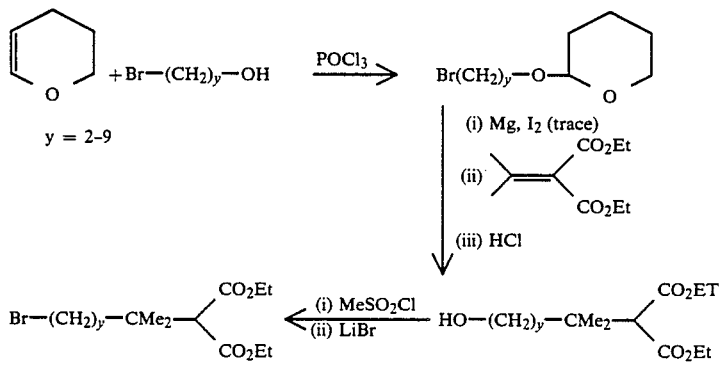

The reactions shown in reaction scheme 1 can be conducted under conditions as described in the Examples or analogous thereto.

Compounds of the formula (I) are useful in the treatment of diseases in which $TXA_2$ is a factor. Thus they would be useful in the treatment of disorders in which aggregation of blood platelets and vasoconstriction play a part.

Particular clinical indications in which the present compounds would be of interest include the treatment or management of post myocardial infarction, coronary thromboses (e.g. in combination with tissue plasminogen activator and other thrombolytics), unstable angina, transient ischaemia, coronary artery bypass grafts, cardiac valve replacement and peripheral and vascular grafts including for example renal transplants.

The compounds of the formula (I) can be administered as the pure compound but it is more usual to administer them as part of a pharmaceutical composition in association with a carrier and one or more excipients. In a further aspect, therefore, the present invention provides a pharmaceutical composition comprising a col, polyvinylpyrrolidone, lecithin, arachis oil, or sesame oil, Such compositions can be administered, for example, by bolus injection or by infusion.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprises a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each such dosage unit suitably contains from 0.1 mg to 1 g, preferably from 0.5 mg to 500 mg, e.g. 10 mg or 20 mg, of a compound of the formula (I) or a pharmaceutically acceptable salt thereof calculated as the compound itself.

A typical daily dosage regimen is 1 mg to 1 g for an average human weighing approximately 70 kg, administered in 1 to 4 dosage units, preferably 1 or 2.

The compositions of this invention, in addition to containing a compound of the formula (I) can also contain other agents: for example one or more agents chosen from phosphodiesterase inhibitors, hypolipidaemic agents, platelet aggregation inhibitors, vasodilators, $\beta$-adrenergic receptor blockers, ACE inhibitors, tissue plasminogen activator and other thrombolytics, and antiarrhythmics.

Particular compositions of this invention are those containing a compound of the formula (I) and a tissue plasminogen activator, and a particular method of administering such compositions is by infusion or bolus injection.

The compositions of the present invention are prepared by bringing the active constituent into association with a pharmaceutically acceptable carrier and optionally other excipients and ingredients as defined above.

As indicated above, compounds of the formula (I) have biological activity that is indicative of an ability to antagonise $TXA_2$ receptors. The $TXA_2$ antagonist activity has been demonstrated in the human platelet binding assay.

The platelet binding assay used was essentially the method described by Mais et al, *J. Pharm. Exp. Ther.*, 1985, 235(3), 729-734 where [$^{125}$I]PTA-OH was used as the receptor ligand.

The $IC_{50}$ values represent the concentration which produces a 50% inhibition of specific [$^{125}$I]PTA-OH binding.

The activities of the compounds of the present invention in the assay are described in Example 33.

The following Examples are illustrative of the invention.

In the Examples, all temperatures are in °C. Melting points are uncorrected and were obtained in an open capillary tube using a Büchi 510 Melting Point Apparatus.

EXAMPLE 1

7-(Benzenesulphonamido)heptanoic Acid

Benzenesulphonyl chloride (7 mmol) was added to a solution of 7-aminoheptanoic acid (7 mmol) in 10% sodium hydroxide solution (10 ml). The mixture was stirred at room temperature for 3 hours. The pH was adjusted to 1 with 2NHCl and the solution was extracted with chloroform (3×100 ml). The chloroform extracts were dried over magnesium sulphate, the solvent was removed and the residue was recrystallised from methanol-water to give 7-(benzenesulphonamido)-heptanoic acid (0.75 g, 38%); m.p. 75°-77° C.

EXAMPLE 2

8-(Benzenesulphonamido)octanoic Acid

Substituting 8-aminooctanoic acid for 7-aminoheptanoic acid in Example 1 and using corresponding molar proportions of other reagents gave 8-(benzenesulphonamido)octanoic acid (0.76 g, 50%) from isopropanol/water; m.p. 82°-84° C.

EXAMPLE 3

8-(4-Chlorobenzenesulphonamido)octanoic Acid

A solution of 4-chlorobenzenesulphonyl chloride (6 mmol) in chloroform (2.5 ml) was added to a solution of 8-aminooctanoic acid (6 mmol) in 10% sodium hydroxide solution (10 ml). The mixture was stirred at room temperature for 24 hours and was then extracted with chloroform (4×40 ml), the chloroform layers being discarded. The aqueous layer was acidified to pH1 with conc. HCl and was extracted with chloroform (4×100 ml). The combined chloroform extracts were then dried (Mg SO$_4$). Concentration and crystallisation from isopropanol-water gave 8-(4-chlorobenzenesulphonamido)-octanoic acid (1.22 g; 58%); m.p. 122°-124° C.

EXAMPLE 4

6-(Benzenesulphonamido)hexanoic Acid

Benzenesulphonyl chloride (10 ml) was added to a stirred solution of 6-aminocaproic acid (8.8 g) in 10% sodium hydroxide solution (50 ml) over 30 minutes. The solution was stirred for 1 hour, acidified with dilute hydrochloric acid and the precipitate was collected by filtration. Recrystallisation from chloroform yielded 6-(benzenesulphonamido)hexanoic acid (10.5 g) as white prisms. m.p. 119°-120° C.

EXAMPLE 5

8-(4-Chlorobenzenesulphonamido)2,2-dimethyloctanoic Acid (i) Ethyl 2,2-dimethyl-8-bromooctanoate A solution of lithium diisopropylamine in cyclohexane (0.15 mol, 100 ml) and tetrahydrofuran (150 ml) was cooled to −60° C. and treated with ethyl isobutyrate (18.59 g, 0.16 mole). The solution was stirred for 1 hour then treated with 1,6-dibromohexane (51.23 g, 0.21 mole), hexamethylphosphoramide (45 g) and was stirred at −70° C. for 1 hour. The solution was then warmed to room temperature and the solvent was removed under reduced pressure. The remaining solution was treated with saturated ammonium chloride solution (400 ml) and extracted with ethylacetate (2×200 ml). The ethyl acetate extracts were combined and washed with dilute hydrochloric acid (100 ml), sodium bicarbonate (100 ml) and then dried over magnesium sulphate. The solvent and unreacted starting material were removed by distillation to give the title compound as an oil.

(ii) Ethyl 8-(4-chlorobenzenesulphonamido)-2,2-dimethyloctanoate

A mixture of 4-chlorobenzenesulphonamide (4.5 g), ethyl 8-bromo-2,2-dimethyloctanoate (3.3 g) and potassium carbonate (9.3 g) in dry methylethylketone (140 ml) was refluxed for 9 hours. The inorganic residues were removed by filtration and the filtrate was evaporated to dryness to give an oil. Chromatography on silica gel eluted with chloroform-petroleum ether 15:1 gave the title compound (1.05 g) as an oil.

(iii) 8-(4-Chlorobenzenesulphonamido)-2,2-dimethyloctanoic Acid

A solution of ethyl 8-(4-chlorobenzenesulphonamido)-2,2-dimethyloctanoate (1.0 g), sodium hydroxide (1.5 g) in ethanol (40 ml) and water (5 ml) was stirred at room temperature for 90 hours then refluxed for 3 hours. The solvent was removed and the residue was dissolved in dilute hydrochloric acid, the resulting solution then being extracted with chloroform (3×50 ml). The combined chloroform extracts were dried over magnesium sulphate, the solvent was removed and the residue was recrystallised from isopropanol-water to give the title compound as a white solid (0.7 g) m.p. 95°–96° C.

| $C_{16}H_{24}NSO_4Cl$ | |
| --- | --- |
| Found: | C 52.87, H 6.77, Cl 10.08, S 8.73 |
| Required: | C 53.10, H 6.68, Cl 9.80, S 8.86 |

Infra-red (Nujol)$\gamma$ (cm$^{-1}$); 3590–2130 (broad, complex series of bands), 3254 (strong, v. sharp), 1702 (v. strong, v. sharp), 1589 and 1575 (weak, sharp), 1330 (v. strong, v. sharp), 1161 (v. strong, v. sharp) N.M.R.; 250 MHz: $\delta$(CDCl$_3$) (ppm): 1.2 (S, 6H), 1.3 (m, 8H), 1.5 (m, 2H), 2.9 (m, 2H), 4.85 (t, 1H), 7.5 (m, 2H), 7.8 (m, 2H).

EXAMPLE 6

9-(4-Chlorobenzenesulphonamido)nonanoic Acid (i) 9-(4-Chlorobenzenesulphonamido)nonanenitrile A solution of 9-aminononanenitrile (2.0 g) in pyridine (60 ml) was treated with 4-chlorobenzenesulphonyl chloride (2.74 g) in portions. The solution was stirred for 18 hours then the solvent was removed in vacuo. The residue was dissolved in dilute hydrochloric acid and extracted with chloroform. The chloroform extract was dried over magnesium sulphate, the solvent was removed and the residue was chromatographed on silica gel eluted with chloroform to give the title compound (0.7 g) as a low melting solid.

(ii) 9-(4-Chlorobenzenesulphonamido)nonanoic Acid 9-(4-Chlorobenzenesulphonamido)nonanenitrile (0.7 g) was dissolved in ethanol (50 ml) and water (10 ml) containing sodium hydroxide (1.5 g). The mixture was refluxed for 20 hours then the solvent was removed. The residue was dissolved in water and treated with hydrochloric acid to give a white precipitate. This was collected by filtration and recrystallised from ethanol-water to give the title compound (0.56 g) m.p. 121°–123° C.

| $C_{15}H_{22}ClNO_4S$ | |
| --- | --- |
| Found: | C 51.73, H 6.38, Cl 10.73, N 4.13, S 8.95 |
| Required: | C 51.79, H 6.37, Cl 10.19, N 4.03, S 9.22 |

Infra-red (Nujol)$\gamma$ (cm$^{-1}$); 3580–2150 (broad, complex series of bands), 3287 (v. strong, v. sharp), 1699 (v. strong, v. sharp), 1588 (medium, sharp), 1574 (weak, sharp), 1331 (v. strong, sharp), 1163 (v. strong, sharp), 834 and 827 (medium, v. sharp). N.M.R.; 250 MHz: $\delta$(CDCl$_3$) (ppm): 1.3 (m, 4H), 1.45 (m, 2H), 1.65 (m, 2H), 2.35 (m, 2H), 2.95 (m, 2H), 4.6 (t, 1H), 7.5 (m, 2H), 7.8 (m, 2H).

EXAMPLE 7

9-(Benzenesulphonamido)nonanoic Acid (i) 9-(Benzenesulphonamido)nonanenitrile

A solution of 9-aminononanenitrile (2.0 g) in pyridine (60 ml) was treated with benzenesulphonyl chloride (2.29 g) in pyridine (10 ml). The solution was stirred for 18 hours when the solvent was removed in vacuo. The residue was dissolved in dilute hydrochloric acid and extracted with chloroform. The chloroform extract was dried over magnesium sulphate, the solvent was removed and the residue was chromatographed on silica gel eluted with chloroform to give the title compound (0.74 g) as a low melting solid.

(ii) 9-(Benzenesulphonamido)nonanoic Acid 9-(Benzenesulphonamido)nonanenitrile (0.72 g) was dissolved in ethanol (50 ml) and water (10 ml) containing sodium hydroxide (1.5 g). The mixture was refluxed for 18 hours then the solvent was removed. The residue was dissolved in water and treated with hydrochloric acid to give a white precipitate. This was collected by filtration and recrystallised from methanol-water to give the title compound (0.52 g) m.p. 82°–84° C.

| $C_{15}H_{23}NO_4S$ | |
| --- | --- |
| Found: | C 57.48, H 7.32, N 4.50, S 9.93 |
| Requires: | C 57.48, H 7.40, N 4.47, S 10.23 |

EXAMPLE 8

7-(4-Chlorobenzenesulphonamido)hept-5-ynoic Acid (i) Methyl 7-phthalimidohept-5-ynoate A mixture or potassium phthalimide (2.31 g) and methyl 7-bromohept-5-ynoate (3.0 g) in dimethylformamide (35 ml) was heated at 110° C. for 4.5 hours. The cooled solution was poured into water (75 ml) and the pH of the solution was adjusted to 6. The resulting solution was extracted with ether (4×200 ml) and the combined ether extracts were dried over magnesium sulphate, the solvent was removed and the residue was chromatographed on silica gel eluted with chloroform to give the title compound (1.56 g) m.p. 62°–63° C.

(ii) 7-Phthalimidohept-5-ynoic Acid

Methyl 7-phthalimidohept-5-ynoate (1.45 g) was dissolved in a mixture of concentrated hydrochloric acid (7.3 ml), acetone (30 ml) and water (14.6 ml) and the resulting solution was heated at reflux for 3.5 hours. The solution was cooled and then poured into water (175 ml). The precipitate was collected by filtration and recrystallised from ethanol-water to give the title compound (1.12 g) m.p. 120°–122° C.

(iii) 7-Aminohept-5-ynoic Acid

Hydrazine hydrate (0.1 ml) was added to a solution of 7-phthalimidohept-5-ynoic acid (0.55 g) in ethanol (25 ml). The mixture was refluxed for 3.5 hours and then the solvent was removed under reduced pressure. The residue was suspended in water (20 ml), the pH of the solution was adjusted to 5, and the solid was collected by filtration. The filtrate was evaporated to dryness and the residue was extracted with ethanol (3×5 ml). The ethanol extracts were cooled (5° C.) and the resulting precipitate was collected to give the title compound (0.19 g) m.p. 180°–183° C.

(iv) 7-(4-Chlorobenzenesulphonamido)hept-5-ynoic Acid

4-Chlorobenzenesulphonyl chloride (0.31 g) in chloroform (2 ml) was added to a rapidly stirred solution of 7-aminohept-5-ynoic acid (0.2 g) and sodium hydroxide (0.21 g) in water (3 ml) and stirring was continued for 24 hours. The solution was extracted with chloroform (4×10 ml). The remaining aqueous layer was cooled, treated with hydrochloric acid and the resulting precipitate was collected by filtration and recrystallised from isopropanol-water to give the title compound (0.085 g). m.p. 91°–93° C.

| $C_{13}H_{14}ClNO_4S$ | |
|---|---|
| Found: | C 49.46, H 4.42, N 4.31 |
| Requires: | C 49.45, H 4.47, N 4.44 |

N.M.R. 250 MHz; δ(CDCl$_3$) (ppm): 1.7 (m, 2H), 2.1 (m, 2H), 2.3 (m, 2H), 3.8 (m, 2H), 4.8 (m, 1H), 7.5 (m, 2H), 7.8 (m, 2H).

EXAMPLE 9

(Z)-7-(4-Chlorobenzenesulphonamido)hept-5-enoic Acid

(i) Methyl (Z)-7-phthalimidohept-5-enoate

A mixture of methyl 7-phthalimidohept-5-ynoate (1.9 g) and Lindlar catalyst (250 mg) in methanol (130 ml) was shaken under an atmosphere of hydrogen at 30 psi for 2.5 hours. The catalyst was removed by filtration and the filtrate was evaporated to dryness. The residue was chromatographed on silica gel eluted with chloroform to give the title compound (1.59 g) as a low melting solid. m.p. 47°–49° C.

(ii) (Z)-7-Phthalimidohept-5-enoic Acid

A solution of methyl (Z)-7-phthalimidohept-5-enoate (1.56 g) in acetone (30 ml), concentrated hydrochloric acid (15 ml) and water (15 ml) was refluxed for 2.5 hours. Water (180 ml) was added and the solution was cooled. The precipitate was collected by filtration to give the title compound (1.2 g). m.p. 86°–88° C.

| $C_{15}H_{15}NO_4$ | |
|---|---|
| Found: | C 65.93, H 5.41, N 5.12 |
| Requires: | C 65.92, H 5.53, N 5.13 |

(iii) (Z)-7-Aminohept-5-enoic Acid

Hydrazine hydrate (0.19 ml) was added to a solution of (Z)-7-phtalimidohept-5-enoic acid (1.05 g) in ethanol (25 ml) and water (5 ml). The solution was refluxed for 3 hours and then the solvent was removed. The residue was suspended in water and the pH of the solution was adjusted to 5. The resulting precipitate was collected by filtration. The filtrate was evaporated to dryness and extracted with ethanol. The ethanol extracts were evaporated to dryness to give the title compound as an oil (0.62 g).

(iv) (Z)-7-(4-Chlorobenzenesulphonamido)hept-5-enoic Acid

A rapidly stirred solution of (Z)-7-aminohept-5-enoic acid (0.61 g), sodium hydroxide (0.51 g) in water (5 ml) was treated with 4-chlorobenzenesulphonyl chloride (0.9 g) in chloroform (2.5 ml). The solution was stirred for 24 hours then evaporated with chloroform (4×15 ml). The aqueous layer was treated with hydrochloric acid to pH=1 and extracted with chloroform (4×40 ml). These chloroform extracts were combined, dried over magnesium sulphate and evaporated to dryness. The residue was recrystallised from isopropanol to give the title compound (0.4 g). N.M.R; 250 MHz; δ(CDCl$_3$) (ppm): 1.7 (m, 2H) 2.05 (m, 2H), 2.35 (m, 2H), 3.6 (t, 2H), 4.9 (t, 1H) 5.3 (m, 1H), 5.45 (m, 1H) 7.45 (m, 2H), 7.8 (m, 2H).

EXAMPLE 10

2,2-Dimethyl-10-(4-chlorobenzenesulphonamido)-decanoic Acid

(i) Ethyl 2,2-Dimethyl-10-bromodecanoate

Using the method described in Example 5(i), 1,8-dibromooctane (27.2 g, 0.1 mol) and ethylisobutyrate (10.44 g, 0.09 mol) were reacted in the presence of lithium diisopropylamide (67 ml, 0.1 mol) and hexamethylphosphoramide (22 g) to give the title compound (4.56 g) as an oil.

(ii) Ethyl-10-(4-chlorobenzenesulphonamido)-2,2-dimethyldecanoate

Ethyl 2,2-dimethyl-10-bromodecanoate (2.2 g, 0.007 mol) was treated with 4-chlorobenzenesulphonamide (2.6 g, 0.014 mol) and potassium carbonate by the method described in Example 5(ii) to give title compound (1.4 g) as an oil.

(iii) 2,2-Dimethyl-10-(4-chlorobenzenesulphonamido)-decanoic Acid

Ethyl-10-(4-chlorobenzenesulphonamido)-2,2-dimethyldecanoate (1.4 g, 0.003 mol) was treated with sodium hydroxide by the method described in Example 5(iii) to give the title compound which was recrystallised from ether/pet. ether (0.59 g, m.p. 78°–9° C.).

| $C_{18}H_{28}ClNO_4S$ | |
|---|---|
| Found: | C 55.32, H 7.29, N 3.51, Cl 9.52 |
| Required: | C 55.44, H 7.24, N 3.59, Cl 9.09 |

EXAMPLE 11

12-(4-Chlorobenzenesulphonamido)-dedecanoic Acid

12-Aminododecanoic acid (2.15 g, 0.01 moles) was treated with 4-chlorobenzenesulphonyl chloride (2.11 g, 0.01 moles) as described in Example 3 to give the title compound (1.8 g, m.p. 144°–6° C.).

EXAMPLE 12

8-(4-Chlorobenzenesulphonamido)-3,3-dimethyloctanoic Acid

(i) 5-Bromopentyltetrahydropyranylether

Three drops of phosphoryl chloride were added to a stirred mixture of 5-bromopentanol (34.3 g, 205 mmol) and dihydropyran (19.0 g, 226 mmol). After standing for one hour, the mixture was fractionated. Yield 34.7 g, b.p. 102° C. (0.2 bar). Chromatography on alumina eluted with petroleum ether gave the pure title compound (25.1 g, 52% of theory) as an oil.

(ii) Diethyl (6-hydroxy-1,1-dimethylhexyl)malonate

At 50° C., a solution of 5-bromopentyltetrahydropyranylether (13.8 g, 58.7 mmol) was dropped slowly into a mixture of magnesium (1.3 g), 30 ml of dry tetrahydrofuran and one crystal of iodone. The resulting Grignard solution was then dropped at −10° C. into a stirred solution of 11.9 g (58.7 mmol) of isopropylidenemalonic acid diethylester in 100 ml of dry tetrahydrofuran. The resulting solution was stirred for one hour at room temperature, poured into a mixture of ice and hydrochloric acid and extracted with ether. After drying over sodium sulphate, the solvent was removed and the oily residue was taken up in ethanol. A small amount of Amberlyst 15 was added and the mixture was heated for 15 minutes at 75° C. After filtration, the solution was evaporated and the oily residue was chromatographed on silica gel with methylene chloride, then eluted with ether. Yield: 10.0 g, (34% of theory), colourless oil.

(iii) Diethyl (6-bromo-1,1-dimethylhexyl)malonate

A solution of diethyl (6-hydroxy-1,1-dimethylhexyl)malonate (5.0 g, 17.3 mmol) in methylene chloride (50 ml) was treated with 2.2 g (19 mmol) of methansulphonyl chloride at −10° C. After one hour, the solution was extracted successively with diluted hydrochloric acid, sodium bicarbonate solution and water, then dried over sodium sulphate and evaporated. The oily residue was taken up in 200 ml of acetone, lithium bromide (5.0 g) was added and the mixture was heated for one hour at 50° C. After removing the solvent, 100 ml water was added and the mixture was extracted with ether. The combined ether extracts were dried over sodium sulphate and the solvent was removed to give 5.3 g (87% of theory) of the title compound as an oil.

(iv) Diethyl [6-(4-chlorobenzenesulphonamido)-1,1-dimethyl)hexyl]malonate

A solution of 6.45 g (30.2 mmol) of dry sodium salt of 4-chlorobenzenesuolphonamide in 50 ml dimethyl formamide was treated for 15 hrs at 70° C. with 5.3 g (15.1 mmol) of diethyl (6-bromo-1,1-dimethylhexyl)malonate. The solution was then poured into water, the mixture was extracted with ether and the ether phase was dried over sodium sulphate. After evaporation of the ether, the oily residue was dissolved in toluene, cyclohexane was added and the precipitated 4-chlorobenzenesulphonamide was filtered off. The filtrate was stirred with silica, filtered and the solvent was evaporated off. Yield: 5.2 g (75% of theory) as an oil.

(v) 8-(4-Chlorobenzenesulphonamido)-3,3-dimethyloctanoic Acid

A mixture of diethyl [6-(4-chlorobenzenesulphonamido)-1,1-dimethyl)hexyl]malonate (5.0 g, 10.8 mmol), 30 ml of 2 N NaOH, 20 ml of water and two drops of Adogen (Trade Mark) was kept for 12 hours at reflux temperature. The mixture was cooled, extracted with ether and was then acidified. The acidic solution was extracted with ethyl acetate and the ethyl acetate solution was dried over sodium sulphate, then evaporated. The oily residue was kept for 20 minutes at 180° C., after which it was dissolved in sodium bicarbonate solution. The aqueous solution was extracted with ether, acidified by means of hydrochloric acid, and was then again extracted with ether. The ether extract was dried over $Na_2SO_4$, the solvent was removed and the residue was purified by chromatography on silica gel with ether. Yield: 2.4 g (61% of theory), wax-like mass.

EXAMPLE 13

7-(4-Chlorobenzenesulphonamido)heptanoic Acid

A solution of 7-aminoheptanoic acid in 10% sodium hydroxide solution was treated with 4-chlorobenzenesulphonyl chloride in the manner of Example 1 to give the title compound which, after recrystallisation from aqueous ethanol, had a melting point of 128°–129° C.

| Calculated for $C_{13}H_{18}ClNO_4S$: | C, 4.82, H, 5.67; |
| --- | --- |
| | N, 4.38; Cl, 11.09; S, 10.03 |
| Found: | C, 48.96; H, 5.72; |
| | N, 4.29, Cl, 11.25; S, 9.98 |

NMR (DMSO-$d_6$, 250 MHz) δ 7.79, 7.68 (2m, 5H, aryl ring H, NH), 2.72 (m, 2H, —NH<u>CH</u>$_2$—), 2.16 (t, 2H, —<u>CH</u>$_2$C═O), 1.43, 1.34 (2m, 4H, —NHCH$_2$<u>CH</u>$_2$—, —<u>CH</u>$_2$CH$_2$C═O) 1.18 (m, 4H, —CH$_2$(<u>CH</u>$_2$)$_2$CH$_2$—).

EXAMPLE 14

8-(3-Chlorobenzenesulphonamido)octanoic Acid

A solution of 8-aminooctanoic acid in 10% sodium hydroxide solution was treated with 3-chlorobenzenesulphonylchloride in the manner of Example 2 to give the title compound which, after recrystallisation from aqueous ethanol, had a melting point of 85°–86° C.

| Calculated for $C_{14}H_{20}ClNO_4S$: | C, 50.37; H, 6.04; N, 4,.20; |
| --- | --- |
| | Cl, 10.62; S, 9.61. |
| Found: | C, 50.52; H, 6.07; N, 4.07; |
| | Cl, 10.69; S, 9.54. |

NMR (DMSO-$d_6$, 250 MHz) δ 7.70, (m, 5H, aryl ring H, NH), 2.77 (m, 2H, —NH<u>CH</u>$_2$—), 2.18 (t, 2H, —<u>CH</u>$_2$. C═O), 1.47, 1.36 (2m, 4H, —NHCH$_2$<u>CH</u>$_2$—, —<u>CH</u>$_2$CH$_2$C═O), 1.21 (m, 6H, —CH$_2$(<u>CH</u>$_2$)$_3$CH$_2$—).

EXAMPLE 15

8-(4-Nitrobenzenesulphonamido)octanoic Acid

A solution of 8-aminooctanoic acid in 10% sodium hydroxide solution was treated with 4-nitrobenzenesulphonyl chloride in the manner of Example 2 to give the title compound which, on recrystallisation from aqueous ethanol, had a melting point of 126°–7° C.

| Calculated for $C_{14}H_{20}N_2O_6S$: | C, 48.83; H, 5.86; N, 8.14; |
| --- | --- |
| | S, 9.31. |
| Found: | C, 48.76; H, 5.94; N, 8.09; S, 9.15. |

NMR (DMSO-$d_6$, 250 MHz) δ 8.42, 804 (2m, 4H, aryl ring H), 7.98 (t, 1H, NH), 2.80 (m, 2H, —NH<u>CH</u>$_2$—), 2.17 (t, 2H, —<u>CH</u>$_2$C═O), 1.43, 1.36 (2m, 4H, —NHCH$_2$<u>CH</u>$_2$—, —<u>CH</u>$_2$CH$_2$C═O), 1.20 (m, 6H, —CH$_2$(<u>CH</u>$_2$)$_3$—CH$_2$).

EXAMPLE 16

8-(4-Bromobenzenesulphonamido)octanoic Acid

A solution of 8-aminooctanoic acid in 10% sodium hydroxide solution was treated with 4-bromobenzenesulphonyl chloride in the manner of Example 2 to give the title compound which, on recrystallisation from aqueous ethanol, had a melting point of 115°–116° C.

| | |
|---|---|
| Calculated for $C_{14}H_{20}BrNSO_4$: | C, 44.45; H, 5.33; N, 3.70, Br 21.12; S, 8.48. |
| Found: | C, 44.49; H, 5.27; N, 3.69; Br, 21.14; S, 8.23 |

NMR (DMSO-$d_6$, 250 MHz), δ 7.81, 7.70 (2m, 5H, aryl ring H, NH), 2.73 (m, 2H, —NHCH$_2$—), 2.18 (t, 2H, CH$_2$C=O), 1.44, 1.33 (2m, 4H, —NHCH$_2$CH$_2$, CH$_2$CH$_2$C=O), 1.18 (m, 6H, —CH$_2$(CH$_2$)$_3$CH$_2$—).

EXAMPLE 17

8-(4-Methoxybenzenesulphonamido)octanoic Acid

A solution of 8-aminooctanoic acid in 10% sodium hydroxide solution was treated with 4-methoxybenzenesulphonylchloride in the manner of Example 2 to give the title compound which, on recrystallisation from aqueous 2-propanol, had a melting point of 102°–103° C.

| | |
|---|---|
| Calculated for $C_{15}H_{23}NSO_5$: | C, 54.69; H, 7.04; N, 4.25; S, 9.73. |
| Found: | C 54.77, H 7.08, N 4.24, S 9.74. |

NMR (DMSO-$d_6$, 250 MHz) δ 7.66, 7.06 (2m, 4H, aryl ring H), 7.34 (t, 1H, NH), 3.78 (s, 3H, CH$_3$O), 2.62 (m, 2H, —NHCH$_2$—), 2.11 (t, 2H, CH$_2$C=O), 1.38, 1.27 (2m, 4H, —NHCH$_2$CH$_2$, —CH$_2$CH$_2$C=O), 1.12 (m, 6H, —CH$_2$(CH$_2$)$_3$CH$_2$—).

EXAMPLE 18

8-(3,4-Dichlorobenzenesulphonamido)octanoic Acid

8-Aminooctanoic acid (1.0 g, 0.006 mol) was treated with 3,4-dichlorobenzenesulphonylchloride (1.54 g, 0.006 mol), according to the method described in Example 4, to give the title compound which was recrystallised from 2-propanol/water (1.2 g, m.p. 115°–6° C.).

| $C_{14}H_{19}Cl_2NO_4S$ | |
|---|---|
| Found: | C 45.65, H 5.23, N 3.81, Cl 19.29, S 8.75 |
| Required: | C 45.66, H 5.20, N 3.81, Cl 19.25, S 8.71 |

EXAMPLE 19

11-(4-Chlorobenzenesulphonamido)undecanoic Acid

11-Aminoundecanoic acid (4.02 g, 0.02 mol) was treated with 4-chlorobenzenesulphonyl chloride (4.22 g, 0.02 mol) as described in Example 4 to give the title compound which was recrystallised from 2-propanol/ether (1.8 g, m.p. 128°–9° C.).

| $C_{17}H_{26}ClNO_4S$ | |
|---|---|
| Found: | C 54.50, H 7.03, N 3.72, Cl 9.54, S 8.46 |
| Required: | C 54.32, H 6.97, N 3.73, Cl 9.43, S 8.53 |

EXAMPLE 20

11-(3-Chlorobenzenesulphonamido)undecanoic Acid

Substituting 3-chlorobenzenesulphonyl chloride for 4-chlorobenzenesulphonyl chloride in Example 19 gave the title compound from 2-propanol/ether (1.9 g, m.p. 116°–7° C.).

| $C_{17}H_{26}ClNO_4S$ | |
|---|---|
| Found: | C 54.40, H 7.03, N 3.78, Cl 9.65, S 8.46 |
| Required: | C 54.32, H 6.97, N 3.73, Cl 9.43, S 8.53 |

EXAMPLE 21

8-(4-Aminooctanoic acid (1.0 g, 0.006 mol) was treated with p-toluene sulphonyl chloride (1.2 g, 0.006 mol) according to the method described in Example 4 to give the title compound which was recrystallised from 2-propanol/water (1.0 g, m.p. 110°–2° C.

| $C_{15}H_{23}NO_4S$ | |
|---|---|
| Found: | C 57.45, H 7.45, N 4.43, S 10.36 |
| Required: | C 57.48, H 7.40, N 4.47, S 10.23 |

EXAMPLE 22

6-(4-Chlorobenzenesulphonamido)hexanoic Acid

6-Aminohexanoic acid (2.62 g, 0.02 mol) was treated with 4-chlorobenzenesulphonyl chloride (4.22 g, 0.02 mol) by the method described in Example 4 to give the title compound which was recrystallised from ethylacetate-ether (1.92 g, m.p. 126°–7° C.

| $C_{12}H_{16}ClNO_4S$ | |
|---|---|
| Found: | C 47.04, H 5.18, N 4.60, S 10.77, Cl 11.60 |
| Required: | C 47.13, H 5.27, N 4.58, S 10.49, Cl 11.60 |

EXAMPLE 23

9-(3-Chlorobenzenesulphonamido)nonanoic Acid (i) 9-(3-Chlorobenzenesulphonamido)nonanenitrile 9-Aminononanenitrile (4.0 g, 0.26 mol) was treated with 3-chlorobenzene sulphonyl chloride (5.5 g, 0.26 mol) by the method described in Example 6(i) to give the title compound (4.4 g, m.p. 42°–3° C.).

(II) 9-(3-Chlorobenzenesulphonamido)nonanoic Acid 9-(3-Chlorobenzenesulphonamido)nonanenitrile (4.4 g, 0.013 mol) was treated with NaOH (5 g, 0.115 mol) in 30 ml water and 50 ml ethanol by the method described in Example 6(ii). Chromatography in CHCl$_3$:MeOH 10:1 on silica and recrystallisation from 2-propanol/pet. ether 60°–80° gave the title compound (0.94 g, m.p. 112°–3° C.).

| $C_{15}H_{22}ClNO_4S$ | |
|---|---|
| Found: | C 51.39, H 6.06, N 4.01, Cl 10.31, S 9.23 |

-continued

| C$_{15}$H$_{22}$ClNO$_4$S | |
|---|---|
| Required: | C 51.79, H 6.37, N 4.03, Cl 10.19, S 9.22 |

EXAMPLE 24

10-(4-Chlorobenzenesulphonamido)decanoic Acid (i) Methyl-10-bromodecanoate

A mixture of 10-bromodecanoic acid (2.0 g, 0.008 mol) methanol (50 ml) and concentrated sulphuric acid (2 ml) was refluxed for 3 hours. After evaporation to dryness the residue was basified with aqueous Na$_2$CO$_3$ and extracted with dichloromethane. Evaporation of the solvent from the extracts yielded the title compound as an oil (1.64 g).

(ii) Methyl-10(4-chlorobenzenesulphonamido)decanoate

A mixture of methyl 10-bromodecanoate (1.5 g, 0.006 mol), 4-chlorobenzenesulphonamide (3.44 g, 0.018 mol), potassium carbonate (6.2 g, 0.045 mol) and dimethylformamide (50 ml) was heated at 100°–120° C. for 3 hours. After cooling, the inorganic material was removed by filtration. The filtrate was evaporated to dryness and the residue was extracted with dichloromethane. The residual oil obtained by evaporation was chromatographed on silica gel in petroleum ether (40°–60° C.) and the solid obtained on evaporation of the eluate was recrystallised (ether-pet. ether 40°–60°) to give the title compound (0.9 g, m.p. 68°–70° C.).

(iii) 10-(4-Chlorobenzenesulphonamido)decanoic Acid

Methyl 10-(4-chlorobenzenesulphonamido)decanoate (0.85 g, 0.0023 mol) was treated with 5N sodium hydroxide (15 ml) in ethanol (25 ml) at room temperature for 1 hour. The pH was adjusted to 1 with dilute hydrochloric acid and the precipitated solid was filtered off and recrystallised (isopropanol-ether) to give the title compound (0.17 g, m.p. 192°–4° C.).

| C$_{16}$H$_{24}$ClNO$_4$S | |
|---|---|
| Found: | C 53.36, H 6.62, N 3.75, Cl 10.01, S 8.77 |
| Required: | C 53.10, H 6.68, N 3.87, Cl 9.80, S 8.86 |

EXAMPLE 25

8(4-Fluorobenzenesulphonamido)octanoic Acid

8-Aminooctanoic acid (1.0 g, 0.006 mol) was treated with 4-fluorobenzenesulphonyl chloride (1.22 g, 0.006 mol) in the presence of sodium hydroxide (0.8 g, 0.019 mol) in 15 ml water, tetrabutylammonium hydroxide (4 drops, 40% solution) and dichloromethane and the resulting mixture was subjected to vigorous stirring for 3 hours. The organic layer was then separated and evaporated to dryness and the residue was recrystallised from 2-propanol-water to give the title compound (0.88 g, m.p. 97°–8° C.).

| C$_{14}$H$_{20}$FNO$_4$S | |
|---|---|
| Found: | C 53.25, H 6.46, N 4.53, S 9.84 |
| Requires: | C 52.98, H 6.35, N 4.41, S 10.10 |

NMR (DMSO-d$_6$, 250 MHz), δ 7.86, 7.45 (2m, 4H, aryl ring H), 7.63 (t, 1H, —NH), 2.74 (m, 2H, —NHC$\underline{H}_2$—), 2.18 (t, 2H, CH$_2$C=O), 1.46, 1.35 (2m, 4H, —NHCH$_2$C$\underline{H}_2$—, C$\underline{H}_2$CH$_2$C=O), 1.20 (m, 6H, —CH$_2$(C$\underline{H}_2$)$_3$CH$_2$—).

EXAMPLE 26

9-(4-Bromobenzenesulphonamido)nonanoic Acid (i) 9-(4-Bromobenzenesulphonamido)nonanenitrile 9-Aminononanenitrile (1.54 g, 0.01 mol) was treated with 4-bromobenzenesulphonychloride (2.56 g, 0.01 mol) by the method described in Example 6(i) to give the title compound (0.7 g) as an oil.

(ii) 9-(4-Bromobenzenesulphonamido)nonanoic Acid 9-(4-Bromobenzenesulphonamido)nonanenitrile (0.6 g, 0.0016 mol) was treated with sodium hydroxide (2 g, 0.05 mol) in 10 ml water plus 20 ml ethanol by the method described in Example 6(ii) to give the title compound (0.35 g, m.p. 124°–5° C.) after recrystallisation from chloroformpetroleum ether 40°–60°.

| C$_{15}$H$_{22}$BrNO$_4$S | |
|---|---|
| Found: | C 45.99, H 5.78, N 3.57, S 8.27 |
| Required: | C 45.92, H 5.65, N 3.57, S 8.17 |

NMR (CDCl$_3$, 250 MHz), δ 7.80, 7.49 (2m, 4H, aryl ring H), 4.79 (t, 1H, —NH), 2.94 (m, 2H, —NHC$\underline{H}_2$—), 1.49 (m, 4H, —NHCH$_2$C$\underline{H}_2$—, —C$\underline{H}_2$C—C=O), 1.24 (m, 10H, —CH$_2$(C$\underline{H}_2$)$_5$CH$_2$—), 1.21 (s, 6H, 2.CH$_3$).

EXAMPLE 27

3,3-Dimethyl-5-(benzenesulphonamido)pentanoic Acid (i) Ethyl 3,3-dimethyl-5-(benzenesulphonamido)pentanoate Benzenesulphonamide (9.6 g, 61.1 mmol) was added to a stirred solution of sodium methoxide (1.6 g, 29.6 mmol) in methanol (100 ml). The clear solution was evaporated to dryness, then dimethyl formamide (100 ml) and ethyl 5-bromo-3,3-dimethyl-pentanoate (7.0 g, 32.8 mmol) were added and the mixture was heated for eight hours at 70° C. The solution was then poured into water (600 ml), the mixture was extracted with ether and the ether phase, after being dried over sodium sulphate, was evaporated. Treatment of the solid residue with a mixture of toluene and cyclohexane (9:1) left most of the unreacted benzenesulphonamide undissolved. After filtration, the solution was evaporated and the residue was purified by chromatography on silica gel with a mixture of methylene chloride and ethanol (98:2). Yield: 4.6 g (50% of theory), oily substance, n$_D^{20}$=1.5083.

(b) 3,3-Dimethyl-5-(benzenesulphonamido)pentanoic Acid

A mixture of ethyl 3,3-dimethyl-5-(benzenesulphonamido)pentanoate (4.4 g, 14.1 mmol), methanol (30 ml) and 2N NaOH (20 ml) was stirred for 5 hours at 60° C. The methanol was then evaporated, the aqueous phase was acidified (diluted HCl) and the oily acid was extracted with methylene chloride. After drying over sodium sulphate the solvent was removed. Yield: 4.0 g (100 % of theory), oily product, n$_D^{20}$=1.5250.

EXAMPLE 28

5-(4-Chlorobenzenesulphonamido)-3,3-dimethylpentanoic Acid (i) Ethyl 5-(4-chlorobenzenesulphonamido)-3,3dimethyl Pentanoate The title compound was prepared according to the method described in Example 27(i).

Yield: 47% of theory; colourless oil, $n_D^{20} = 1.5162$.

(ii) 5-(4-Chlorobenzenesulphonamido)-3,3-dimethylpentanoic Acid

The title compound was prepared according to the method described in Example 27(ii).

Yield: 93% of theory; m.p. 107°–108° C.

EXAMPLE 29

8-(5-Chloro-2-thienylsulphonamido)octanoic Acid

8-Aminocaprylic acid (1.0 g, 0.006 mole) was treated with 5-chloro-2-thiophene sulphonyl chloride (1.37 g, 0.0063 mole) according to the method described in Example 4 to give the title compound after recrystallisation from isopropanol/water (1.39 g, m.p. 108°–9° C.).

| $C_{12}H_{18}ClNO_4S_2$ | |
|---|---|
| Found: | C 42.46, H 5.39, N 4.11, Cl 10.49, S 19.02 |
| Required: | C 42.41, H 5.34, N 4.12, Cl 10.43, S 18.87 |

EXAMPLE 30

9-(4-Chlorophenylsulphonamido)-2,2-dimethylnonanoic Acid (i) Ethyl 2,2-dimethyl-9-bromononanoate Using the method described in Example 5(i), 1.7 dibromoheptane (25.8 g, 0.1 mol) and ethylisobutyrate (10.4 g, 0.09 mol) were reacted in the presence of lithium diisopropylamide (0.1 mol) and hexamethylphosphoramide (22 g) to give the title compound (24.7 g) as an oil.

(ii) Ethyl-9-(4-chlorobenzenesulphonamido)-2,2-dimethylnonanoate

Ethyl 2,2-dimethyl-9-bromononanoate (2.0 g, 0.007 mol) was treated with 4-chlorobenzenesulphonamide (3.44 g, 0.018 mol) and potassium carbonate (6.2 g, 0.045 mol) by the method described in Example 5(ii) to give the title compound (1.5 g) as an oil.

(iii) 9-(4-Chlorophenylsulphonamido)-2,2-dimethylnonanoic Acid

Ethyl-9-(4-chlorobenzenesulphonamido)-2,2-dimethyl nonanoate (1.4 g, 0.0033 mol) was treated with sodium hydroxide by the method described in Example 5(iii) to yield the title compound which was recrystallised from water (1.09 g, m.p. 89°–90° C.).

| $C_{17}H_{26}ClNO_4S$ | |
|---|---|
| Found: | C 54.33, H 7.18, N 3.90, Cl 9.81, S 8.76 |
| Requires: | C 54.32, H 6.97, N 3.73, Cl 9.43, S 8.53 |

EXAMPLE 31

7-(4-Chlorophenylsulphonamido)-2,2-dimethylheptanoic Acid (i) Ethyl-2,2-dimethyl-7-bromoheptanoate Using the method described in Example 5(i). 1,5-dibromopentane (23 g, 0.1 mol) and ethylisobutyrate (10.4 g, 0.09 mol) were reacted in the presence of lithium diisopropylamide (0.1 mol) and hexamethylphosphoramide (22 g) to give the title compound as an oil (7.4 g).

(ii) Ethyl-7-(4-chlorophenylsulphonamido)-2,2-dimethylheptanoate

Ethyl-2,2-dimethyl-7-bromoheptanoate (7.0 g, 0.026 mol) was treated with 4-chlorobenzenesulphonamide (9.9 g, 0.052 mol) and potassium carbonate (21.5 g, 0.016 mol) by the method described in Example 5(ii) to give the title compound (1.3 g) as an oil.

(iii) 7-(4-Chlorophenylsulphonamido)-2,2-dimethylheptanoic Acid

Ethyl-7-(4-chlorophenylsulphonamido)-2,2-dimethylheptanoate (3.5 g, 0.09 mol) was treated with sodium hydroxide by the method described in Example 5(iii) to give the title compound (1.9 g) m.p. 132°–3° C. (dichloroethane/40°–60° petroleum ether).

| $C_{15}H_{22}ClNO_4S$ + 2% $CH_2Cl_2$ | |
|---|---|
| Found: | C 50.81, H 6.25, N 3.86, Cl 11.65 |
| Requires: | C 51.20, H 6.29, N 3.95, Cl 11.86 |

EXAMPLE 32

8-(2,5-Dichloro-3-thienylsulphonamido)octanoic Acid

8-Aminocaprylic acid (1.0 g, 0.006 mole) was treated with 2,5-dichloro-3-thiophene sulphonyl chloride (1.58 g, 0.006 mole) according to the method described in Example 4 to give the title compound after recrystallisation from isopropanol/water (1.1 g, m.p. 92°–93° C.).

| $C_{12}H_{17}Cl_2NO_4S_2$ | |
|---|---|
| Found: | C 38.30, H 4.55, N 3.81, Cl 18.77 |
| Required: | C 38.50, H 4.58, N 3.74, Cl 18.94 |

Example 33
Platelet Binding Activity
Inhibition of [$^{125}$I]PTA-OH Binding to Washed Human Platelets

| Compound of Example No. | $IC_{50}(\mu M)$ |
|---|---|
| 1 | 2.3 |
| 2 | 0.29 |
| 3 | 0.03 |
| 4 | 61 |
| 5 | 0.15 |

Example 33
Platelet Binding Activity
Inhibition of [$^{125}$I]PTA-OH Binding to Washed Human Platelets

| Compound of Example No. | IC$_{50}$($\mu$M) |
|---|---|
| 6 | 0.018 |
| 7 | 0.28 |
| 8 | 5.4 |
| 9 | 1.6 |
| 10 | 0.47 |
| 11 | 7 |
| 12 | 0.6 |
| 13 | 0.27 |
| 14 | 0.16 |
| 15 | 0.11 |
| 16 | 0.02 |
| 17 | 0.3 |
| 18 | 0.07 |
| 19 | 0.6 |
| 20 | 1.9 |
| 21 | 0.075 |
| 23 | 0.25 |
| 24 | 0.06 |
| 25 | 0.22 |
| 26 | 0.04 |
| 29 | 0.04 |
| 30 | 0.36 |
| 31 | 0.33 |
| 32 | 0.65 |

What is claimed is:

1. A method for the treatment of thromboxane mediated diseases which comprises the administration to a patient of a non-toxic effective thromboxane A$_2$ antagonist amount of a compound of the formula (I):

$$RSO_2NR'BCO_2H \tag{I}$$

or a salt or ester thereof, wherein R is a phenyl, furan or thiophene ring optionally substituted by one or more substituents which are the same or different and are chosen from halogen, nitro, cyano, trifluoromethyl, C$_{1-4}$alkyl and C$_{1-4}$alkoxy; R' is hydrogen or C$_{1-4}$alkyl; and B is an acyclic hydrocarbon group having 4 to 11 linear carbon atoms, any one or more of the linear carbon atoms of which are optionally substituted by one or two C$_{1-3}$alkyl groups.

2. A method according to claim 1 wherein B has at least 6 linear carbon atoms.

3. A method according to claim 2 wherein B is selected from (CH$_2$)$_6$, (CH$_2$)$_7$, (CH$_2$)$_8$, (CH$_2$)$_9$, (CH$_2$)$_5$C(CH$_3$)$_2$, (CH$_2$)$_6$C(CH$_3$)$_2$, (CH$_2$)$_7$C(CH$_3$)$_2$ and (CH$_2$)$_8$C(CH$_3$)$_2$.

4. A method according to claim 1 wherein R is phenyl substituted at the 3- and/or 4-positions by chlorine, bromine, fluorine, nitro, methoxy or methyl.

5. A method according to claim 1 wherein R is 2-thienyl substituted at the 5-position by 5-chloro, 5-bromo or 5-methyl.

* * * * *